United States Patent
Simanzhenkov et al.

(10) Patent No.: US 12,371,396 B2
(45) Date of Patent: Jul. 29, 2025

(54) CATALYTIC CONVERSION OF CARBON DIOXIDE

(71) Applicant: NOVA CHEMICALS (INTERNATIONAL) S.A., Fribourg (CH)

(72) Inventors: Vasily Simanzhenkov, Calgary (CA); Shahin Goodarznia, Calgary (CA); Bolaji Olayiwola, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 628 days.

(21) Appl. No.: 17/642,774

(22) PCT Filed: Sep. 24, 2020

(86) PCT No.: PCT/IB2020/058948
§ 371 (c)(1),
(2) Date: Mar. 14, 2022

(87) PCT Pub. No.: WO2021/064527
PCT Pub. Date: Apr. 8, 2021

(65) Prior Publication Data
US 2022/0396541 A1 Dec. 15, 2022

Related U.S. Application Data

(60) Provisional application No. 62/907,942, filed on Sep. 30, 2019.

(51) Int. Cl.
*C07C 51/00* (2006.01)
*B01J 8/06* (2006.01)
*B01J 23/28* (2006.01)
*C07C 1/12* (2006.01)

(52) U.S. Cl.
CPC ............ *C07C 51/00* (2013.01); *B01J 8/06* (2013.01); *B01J 23/28* (2013.01); *C07C 1/12* (2013.01); *C07C 2523/648* (2013.01); *C07C 2523/88* (2013.01); *C07C 2527/057* (2013.01)

(58) Field of Classification Search
CPC ..... C07C 51/00; C07C 1/12; C07C 2523/648; C07C 2523/88; C07C 2527/057; C07C 53/08; C07C 9/06; C07C 11/04; B01J 23/28
See application file for complete search history.

(56) References Cited

U.S. PATENT DOCUMENTS

2018/0272303 A1* 9/2018 Simanzhenkov ........ B01J 8/025
2018/0273459 A1* 9/2018 Shimizu .................. C07C 51/12

FOREIGN PATENT DOCUMENTS

EP    3369722 A1    9/2018
JP    H 07188096 A  7/1995

OTHER PUBLICATIONS

Yuichi et al, direct production of acetic acid from carbon dioxide, (JPH07188096A machine translation), Jul. 25, 1995.*

(Continued)

*Primary Examiner* — Jafar F Parsa
(74) *Attorney, Agent, or Firm* — Fish & Richardson P.C.

(57) ABSTRACT

A system and method for converting carbon dioxide into products by contacting the carbon dioxide with catalyst in the presence of hydrogen in a reactor.

13 Claims, 4 Drawing Sheets

(56) References Cited

OTHER PUBLICATIONS

International Preliminary Report on Patentability in International Appln. No. PCT/IB2020/058948, mailed on Apr. 5, 2022, 6 pages.
International Search Report and Written Opinion in International Appln. No. PCT/IB2020/058948, mailed on Dec. 18, 2020, 9 pages.

* cited by examiner

CATALYTIC CONVERSION OF CARBON DIOXIDE

CROSS-REFERENCE TO RELATED APPLICATION

This application is a National Stage Application under 35 U.S.C. § 371 and claims the benefit of International Application No. PCT/IB2020/058948, filed Sep. 24, 2020, which claims priority to U.S. Ser. No. 62/907,942, filed on Sep. 30, 2019. The disclosure of the prior application is considered part of and is incorporated by reference in the disclosure of this application.

TECHNICAL FIELD

This disclosure relates to catalytic conversion of carbon dioxide in the presence of hydrogen into acetic acid or carbon monoxide.

BACKGROUND ART

Catalytic oxidative dehydrogenation of alkanes into corresponding alkenes is an alternative to steam cracking. In contrast to steam cracking, oxidative dehydrogenation (ODH) may operate at lower temperature and generally does not produce coke. For ethylene production, ODH can provide a greater yield for ethylene than does steam cracking. The ODH may be performed in a reactor vessel having catalyst for the conversion of an alkane to a corresponding alkene.

Carbon dioxide may be generated in the conversion of lower alkanes (e.g., ethane) into corresponding alkenes (e.g., ethylene). Carbon dioxide ($CO_2$) is the primary greenhouse gas emitted through human activities.

SUMMARY OF INVENTION

An aspect relates to a method of processing carbon dioxide including contacting carbon dioxide with catalyst in presence of hydrogen in a reactor to convert carbon dioxide into acetic acid and carbon monoxide. The method includes discharging a product effluent from the reactor to a condenser heat exchanger. The product effluent includes at least acetic acid, carbon monoxide, and water. The method includes condensing the acetic acid and the water in the condenser heat exchanger.

Another aspect relates to a method of processing carbon dioxide in a reactor system, including contacting carbon dioxide with catalyst in presence of hydrogen in a reactor to convert carbon dioxide to acetic acid, carbon monoxide, ethane, and ethylene. The method includes discharging a product effluent from the reactor to a condenser (a heat exchanger). The product effluent includes at least acetic acid, carbon monoxide, ethane, and ethylene, water, carbon dioxide, and hydrogen. The method includes condensing the acetic acid and the water in the condenser.

Yet another aspect relates to a system to convert carbon dioxide into products including value-added products. The system includes a reactor having an ODH catalyst to convert carbon dioxide in presence of hydrogen into acetic acid and carbon monoxide, and discharge a product effluent including at least acetic acid, carbon monoxide, water, and unreacted carbon dioxide. The system includes a condenser to receive the product effluent and condense acetic acid and water. The heat exchanger is configured to discharge a liquid product stream including at least acetic acid and water and a gas product stream including at least carbon monoxide and unreacted carbon dioxide.

The details of one or more implementations are set forth in the accompa-nying drawings and the description below. Other features and advantages will be apparent from the description and drawings, and from the claims.

BRIEF DESCRIPTION OF DRAWINGS

Like reference numbers and designations in the various drawings indicate like elements.

DESCRIPTION OF EMBODIMENTS

Embodiments of the present techniques are directed to converting carbon dioxide (CO2) in the presence of hydrogen (H2) to acetic acid (C2H4O2) or carbon monoxide (CO). A reactor having catalyst (e.g., ODH catalyst) performs the conversion. While certain ODH catalysts can be employed, the CO2 conversion reactor may generally avoid performing an ODH reaction or significant ODH reactions with the ODH catalyst present. Instead, the ODH catalyst may facilitate reactions (e.g., hydrogenation of CO2) other than ODH, as discussed below. Further, the CO2 conversion can be performed without hydrocarbon feed to the reactor. The ODH catalyst(s) employed may be labeled an "ODH" catalyst because the catalyst can be utilized in other processes to perform ODH to convert lower alkanes to corresponding alkenes. Embodiments of the present reactor may relate to the catalytic hydrogenation of CO2 into acetic acid or carbon monoxide, or both.

The primary product of the CO2 conversion may be acetic acid in presence of feed water (H2O) in the reactor. The primary product of the conversion may be CO in absence of feed H2O in the reactor. The CO2 in the feed to the reactor can be from an integrated system, such as an ethane steam-cracking system, an ODH reactor system that converts ethane to ethylene, and so on. The CO2 conversion reactor that converts CO2 may be labeled as an ODH reactor when the reactor has ODH catalyst (for the CO2 conversion) and not necessarily because the reactor performs an ODH reaction.

The ODH catalyst may be a low-temperature ODH catalyst that provides for the conversion with reactions at less than 425° C. or less than 400° C. As discussed below, reactions in the present CO2 conversion reactor that convert the CO2 may include (1) CO2 hydrogenation, and (2) water gas shift. The reactions are via a catalyst, which can be an ODH catalyst in certain embodiments.

Advantages of the present techniques may include converting CO2 emissions into value-added products. Implementations may provide opportunity to integrate and convert CO2 emissions from steam cracking systems or ODH reactor systems (that convert a lower alkane to a corresponding alkene) into desirable products, such as acetic acid or CO.

Figure 1:
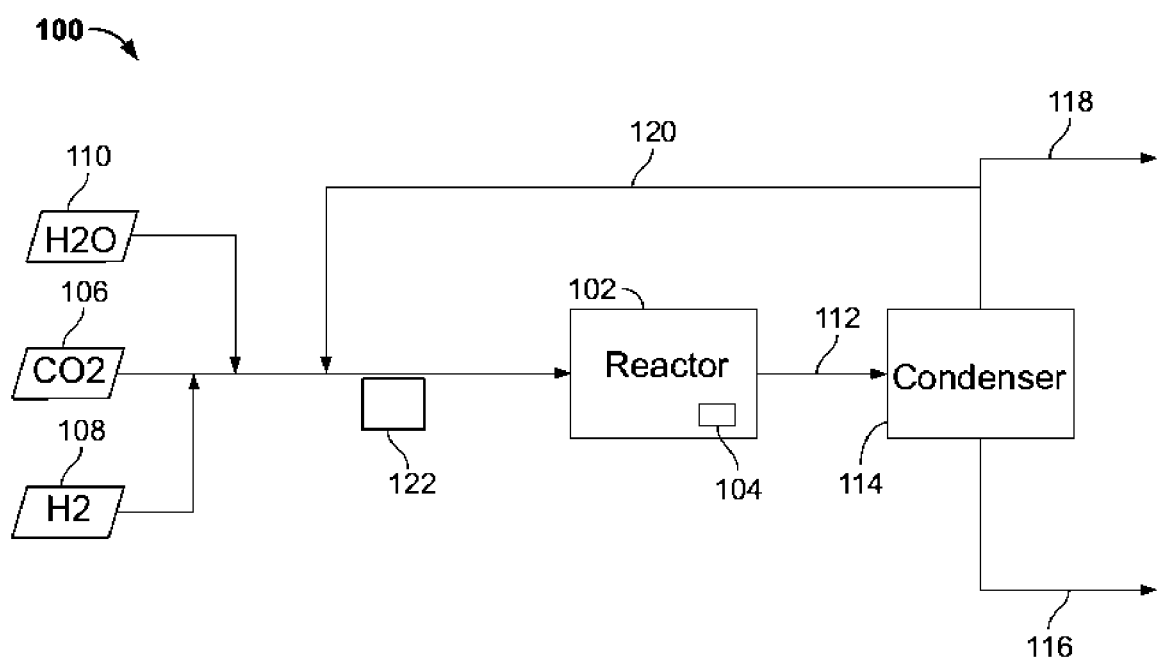
FIG. 1 is a block diagram of a reactor system having a reactor with catalyst for the conversion of CO2 into acetic acid or carbon monoxide (CO).

FIG. 1 is a reactor system 100 having a CO2 converter or CO2 conversion reactor 102 with a catalyst 104 for the conversion of CO2 into acetic acid or CO. The catalyst 104 may be an ODH catalyst. In certain embodiments, the CO2 conversion reactor 102 can resemble aspects of a conventional ODH reactor that converts ethane to ethylene. The CO conversion reactor 102 is configured to receive CO2, H2, and $H_2O$ as feed. In contrast, a conventional ODH reactor employing ODH catalyst receives lower alkanes (e.g., ethane), oxygen, and diluent as feed.

The CO2 converter or conversion reactor 102 may be a fixed-bed reactor (e.g., a tubular fixed-bed reactor), a fluidized-bed reactor, an ebullated bed reactor, or a heat-exchanger type reactor, and so on. The CO2 conversion reactor system 100 may utilize a heat-transfer fluid for controlling temperature of the reactor 102. The heat-transfer fluid may be employed to add heat or remove heat from the CO2 conversion reactor 102 or from the reactor system 100. The heat transfer fluid can be, for example, steam, water (including pressurized or supercritical water), oil, or molten salt, and so forth.

The reactions collectively in the reactor 102 to convert CO2 are typically endothermic. Therefore, the heat transfer fluid is a heating medium. For alternate embodiments with the reactions collectively in the reactor 102 to convert CO2 as exothermic, the heat transfer fluid is a cooling medium. The heating medium and the cooling medium (if employed) may be the same or different type of heat transfer fluid. Lastly, in some implementations, the heat transfer fluid may be a cooling medium or heating medium when the reactor 102 is not in normal operation or is offline or shut down for maintenance activity. In a particular implementation, the heat transfer fluid as a cooling medium may be employed during online regeneration of the catalyst 104.

For a fixed-bed reactor, reactants may be introduced into the reactor at one end and flow past an immobilized catalyst. Products are formed and an effluent having the products may discharge at the other end of the reactor. The fixed-bed reactor may have one or more tubes (e.g., metal tubes, ceramic tubes, etc.) each having a bed of catalyst and for flow of reactants. For the reactor 102, the flowing reactants may be CO2, H2, and optionally H2O. The tubes may include, for example, a steel mesh. Moreover, a heat-transfer jacket adjacent the tube(s) or an external heat exchanger (e.g., feed heat exchanger or recirculation heat exchanger) may provide for temperature control of the reactor. The aforementioned heat transfer fluid may flow through the reactor jacket or external heat exchanger (e.g., shell-and-tube heat exchanger).

In other embodiments, the reactor 102 is a fluidized bed reactor. In implementations, a fluidized bed reactor may have a support for the ODH catalyst. The support may be a porous structure or distributor plate and disposed in a bottom portion of the reactor. Reactants may flow upward through the support at a velocity to fluidize the bed of ODH catalyst. The reactants (e.g., CO2, H2, and optionally H2O for the reactor 102) are converted to products (e.g., acetic acid or CO in the reactor 102) upon contact with the fluidized catalyst. An effluent having products may discharge from an upper portion of the reactor. The fluidized bed reactor may have heat-transfer tubers, a jacket, or an external heat exchanger (e.g., feed heat exchanger or recirculation loop heat exchanger) to facilitate temperature control of the reactor. The aforementioned heat transfer fluid may flow through the reactor tubers, jacket, or external heat exchanger.

The fluidized bed reactor can be (1) a non-circulating fluidized bed, (2) a circulating fluidized bed with regenerator, or (3) a circulating fluidized bed without regenerator. In the conversion of CO2 to acetic acid or CO, catalyst regeneration may not be typically needed and, therefore, a circulating fluidized-bed platform with regenerator may not be implemented in certain embodiments. However, in practice of embodiments with a reactor for dual purposes such as (1) CO2 conversion, and (2) ethane ODH, a circulating fluidized bed with regenerator may be employed. If so, the downcomers to the catalyst regenerator section may be closed during operation of the reactor in the mode of CO2 conversion.

The catalyst 104 may be operated as a fixed bed or fluidized bed. In some implementations, the catalyst 104 in the CO2 conversion reactor 102 is a first low-temperature ODH catalyst that includes molybdenum, vanadium, tellurium, niobium, and oxygen, wherein the molar ratio of molybdenum to vanadium is from 1:0.12 to 1:0.49, the molar ratio of molybdenum to tellurium is from 1:0.01 to 1:0.30, the molar ratio of molybdenum to niobium is from 1:0.01 to 1:0.30, and oxygen is present at least in an amount to satisfy the valency of any present metal elements. The molar ratios of molybdenum, vanadium, tellurium, niobium can be determined by inductively coupled plasma mass spectrometry (ICP-MS). The catalyst may be low temperature in providing for CO2 conversion reactions at less than 425° C. or less than 400° C. This ODH catalyst can be implemented in the reactor 102 without ODH reactions but instead with reactions for the CO2 conversion. The catalyst is available from NOVA Chemicals Corporation having headquarters in Calgary, Canada.

Another example of the catalyst 104 is a second low-temperature ODH catalyst that is a mixed metal oxide having the formula $Mo_aV_bTe_cNb_dPd_eO_f$, where a, b, c, d, e, and f subscripts are relative atomic amounts of the elements Mo, V, Te, Nb, Pd, O, respectively. When a=1, then b=0.01 to 1.0, c=0.01 to 1.0, d=0.01 to 1.0, 0.00≤e≤0.10, and f is a number to satisfy the valence state of the catalyst. The number f may be a number to satisfy at least the valence state of the corresponding elements in the catalyst. This catalyst may provide for the CO2 conversion reaction(s) to occur at a temperature of less than 400° C. or less than 425° C. This catalyst is also available from NOVA Chemicals Corporation having headquarters in Calgary, Canada.

The CO2 conversion reactor 102 may have ODH catalyst and may be similar to a conventional ODH reactor that receives ethane, oxygen, and diluent and converts ethane to ethylene. However, the CO2 conversion reactor 102 may be situated and configured to not receive hydrocarbon or ethane for CO2 conversion, but instead to receive CO2, H2, and optionally H2O as feed and with a focus to produce acetic acid or CO via the ODH catalyst (and not produce significant amounts of ethylene). The present reactor system 100 includes conduits (piping) to route CO2 and H2 (and optionally H2O) to a feed inlet nozzle(s) on the CO2 conversion reactor 102.

A conduit may route the CO2 from a vessel storing CO2 or from a pipeline or conduit header conveying CO2. A source of the CO2 may be, for example, a steam-cracker furnace system (e.g., from flue gas of a steam cracker furnace) or from an ODH system that converts a lower alkane(s) to a corresponding alkene. For instance, the CO2 source may be an amine tower in the in the steam cracker furnace system or in the conventional ODH system. Thus, the reactor system 100 may facilitate reduction of CO2 emissions associated with those sources. Other sources of CO2 are applicable.

A conduit may route the H2 to the CO2 conversion reactor 102 from a vessel storing H2 or from a pipeline or conduit header conveying H2. The source of H2 may be, for example, a demethanizer distillation column or associated system. Other petrochemical sources of H2, as well as water splitting, etc., are applicable sources of H2.

A conduit may route the H2O from, for example, a steam header or steam subheader. In implementations, the steam as the entering H2O 110 is low pressure steam at 150 pounds per square inch gauge (psig) or less. The steam may be, for instance, low pressure steam generated within a conventional ODH system or with a steam cracker system. When acetic acid production is favored, a valve on the conduit conveying the H2O 110 (e.g., steam) may be in an open position to allow the steam 110 to flow to and enter the CO2 conversion reactor 102. In implementations, liquid water is not added and liquid water does not come in contact with the catalyst bed so to avoid pulverizing the catalyst particles. Instead, steam 110 may generally be added.

The CO2 conversion reactor 102 may also be arranged or configured differently than a conventional ODH reactor with respect to reactor temperature control or in the heating or cooling of the reactor. The conversion of ethane to ethylene in an ODH reactor may be generally exothermic. In contrast, the conversion of CO2 to acetic acid or CO in the CO2 conversion reactor 102 may be endothermic. In some implementations of the reactor 102 as an endothermic reactor that is a tubular fixed-bed reactor, the CO2 conversion reactor 102 may be configured with a preheater heat exchanger or with a reactor vessel jacket receiving a heating medium (e.g., steam or oil). Conversely, a conventional ODH reactor that is a tubular reactor may rely on receiving a cooling medium (e.g., oil or molten salt) to the reactor vessel jacket. Other reaction conditions and reactor configurations are applicable.

In operation, the CO2 conversion reactor 102 receives feed that includes carbon dioxide 106 and hydrogen 108. As indicated, the feed to the reactor 102 may also include H2O 110, such as steam. Exemplary reactions in the ODH reactor 102 include [1] and [2] below:

[1] reaction 1 (CO2 hydrogenation): 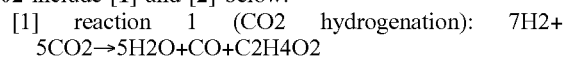 7H2+5CO2→5H2O+CO+C2H4O2

[2] reaction 2 (water gas shift): 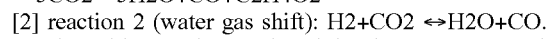 H2+CO2 ↔H2O+CO.

Acetic acid may be produced in the reactor 102 by hydrogenation of CO2 reaction as given in a bulked reaction 1 above. CO may be produced in the reactor 102 by water gas shift reaction as given in reaction 2 above. The presence of H2O in the feed to the reactor 102 may suppress the CO formation by pushing the water gas shift reaction (reaction 2) back towards CO2 formation. Thus, the presence of H2O in the feed may favor the production of acetic acid in reaction 1. The absence of H2O in the feed may favor the production of CO. In either case, CO2 emissions may be reduced in source systems that provide CO2 as feed to the reactor 102 in certain implementations.

Reaction 1 is a bulked reaction that is the sum of multiple intermediate reactions. There may be as many as five reactions that sum to give the bulk reaction depicted as reaction 1. The reaction 1 may be labeled as a simplified bulked reaction and with the actual reaction scheme more complex. Furthermore, the bulked reaction 1 does not represent the only bulked reaction that can explain acetic acid generation from H2 and CO2.

The effluent 112 (e.g., product effluent) from the CO2 conversion reactor 102 may discharge to a condenser 114 in the reactor system 100. The motive force for flow of the effluent 112 to the condenser may be by pressure differential between the reactor 102 and the condenser 114, and/or by a compressor (e.g., positive displacement or dynamic) disposed along the conduit conveying the effluent 112 to the condenser, and the like. In certain implementations, the flow of the effluent 112 may be modulated by the compressor (if employed) or by a control valve (not shown) along the conduit conveying the effluent 112 to the condenser 114. The control valve may control the flow rate (e.g., mass flow rate or volumetric flow rate) of the effluent 112. In some embodiments, the control valve (if employed) may function as a backpressure regulator in controlling pressure in the reactor 102.

The effluent 112 generally has products from the CO2 conversion reactor 102. The effluent 112 may include acetic acid and CO. With presence of H2O in the feed to the reactor 102, the acetic acid may be the main or primary product in the effluent 112. With absence of H2O in the feed to the reactor 102, the CO may be the main or primary product in the effluent 112. Additional products in the effluent 112 may include ethane (C2H6) as a third product and ethylene (C2H4) as a fourth product. The effluent 112 may also include CO2 (unreacted feed), H2 (unreacted feed), H2O (diluent), and other compounds.

The condenser 114 may be an air-cooler heat exchanger, a water-cooler heat exchanger, a quench tower or scrubber column, and so forth. In some implementations, the condenser 114 is a shell-and-tube heat exchanger. If so, a heat-transfer (cooling) fluid may flow through the shell side and the effluent 112 flows the tube side. On the other hand, the heat transfer fluid may flow through the tube side and the effluent 112 flows through the shell side. In particular implementations, the heat transfer fluid may be water, such as cooling tower water.

In operation in the condenser 114 as a heat exchanger, heat is transferred from the effluent 112 to the heat transfer fluid. Components in the effluent 112 may condense due to the heat transfer. The amount of heat transfer and condensation conditions may be affected by the temperature and flow rate of the cooling fluid. The effluent 112 discharging from the condenser 114 may be separated into liquid components 116 and gas components 118. The liquid components 116 can be acetic acid and H2O, which can be separated. Acetic acid can be separated from water, for example, by azeotropic distillation, liquid-liquid extraction, and other separation techniques. The acetic acid can be sold, such as in glacial or dilute form.

The gas components 118 can include CO (main product in absence of H2O feed to reactor 102), C2H6 (3rd product), C2H4 (4th product), CO2 (unreacted feed), and H2 (unreacted feed). The gas components 118 may be separated and sold or sent to adjacent systems.

In implementations, the gas components 118 may be sent to downstream of an acetic acid scrubber in an ODH system that converts ethane to ethylene. For example, the gas components 118 may be sent to a separation train downstream of the acetic acid scrubber. In other implementations, the gas components 118 may be sent to downstream of a quench tower in a steam cracker system that converts ethane to ethylene. For example, the gas components 118 may be sent to a separation train downstream of the acetic acid scrubber. The separation train in either the ODH system or the steam cracker system may include, for instance, an amine tower, a caustic tower (e.g., that removes CO2), a demethanizer distillation (e.g., that separates H2/CO/CH4 from C2H6/C2H4), and a C2 splitter distillation column (e.g., that separates C2H6 from C2H4). Other configurations of the separation train are applicable.

Gas components 118 may be recycled (optional) to the reactor 102 as recycle 120 though a recycle conduit. A portion of the gas components 118 stream may be sent as recycle 120 to the reactor 102. The recycle 120 of the gas components 118 may increase conversion of CO2 by the reactor 102 and reactor system 100. In implementations, the recycle 120 may be added to the feed entering the reactor 102. The motive force for flow of the recycle 120 may be via a compressor (e.g., positive displacement or dynamic) disposed along the recycle conduit, or via a compressor upstream of the condenser 114, and so on. In some applications, the compressor may be low differential pressure blower labeled as a blower. Motive force may be provided without a compressor, such as by an ejector, eductor, jet, injection of motive fluid, and the like, such as where a carrier fluid is available to operate the devices.

Lastly, the feed to the CO2 conversion reactor 102 may be heated via a preheater 122. In certain embodiments, the preheater 122 is a heat exchanger, such as a shell-and-tube heat exchanger or other type of heat exchanger. The heating medium can be steam or oil, and the like.

Figure 4:
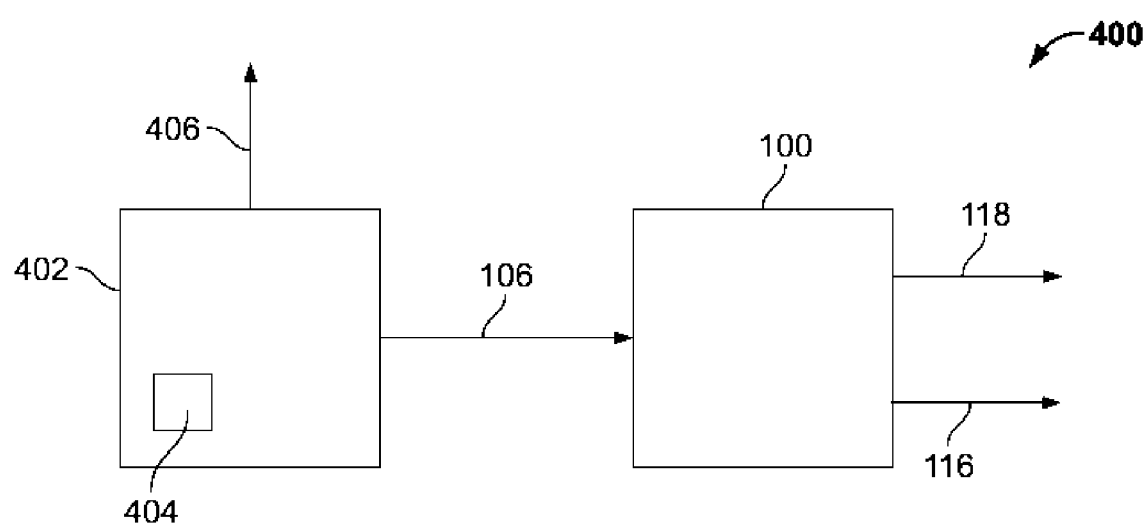
FIG. 4 is a block diagram of integrated systems.

The source of heat or energy for the preheating can be from an integrated system (e.g., system 400 in FIG. 4). The source of heat or energy for the preheating can be, for example, ODH reaction heat from an adjacent ODH reactor system that converts ethane to ethylene. Thus, in those implementations, an adjacent ODH reactor system can provide heat to drive the CO2 conversion reaction in the present reactor system. In other embodiments, a source of heat or energy for the preheating can be, for example, from a steam cracking furnace that converts ethane to ethylene. For instance, a stack of tubes can be placed on the top of convection section of the steam cracking furnace to recover heat from furnace off gas to provide heat or energy to the present CO2 conversion reactor system. Other sources of waste heat may be applicable for preheating the feed to the CO2 conversion reactor.

As indicated, both acetic acid and CO may be desired products. CO can be utilized (e.g., combusted) to generate steam. In addition, CO can be mixed with H2 to give synthesis gas (syngas). Syngas can then be converted to hydrocarbon-based fuels or methanol. There can be markets for methanol in various industries, such as plastic, automotive, paints and adhesives, construction, and pharmaceutical.

Acetic acid may be converted to vinyl acetate as a comonomer for polyvinylchloride copolymer production. Acetic acid may be converted to ethanol via hydrogenation reaction for use of the ethanol, for example, as fuel. Further, acetic acid may be converted to ethylene. For example, ethylene may be produced via a two-stage process of acetic acid hydrogenation followed by ethanol dehydration for use of the ethylene in polyethylene synthesis.

Figure 2:
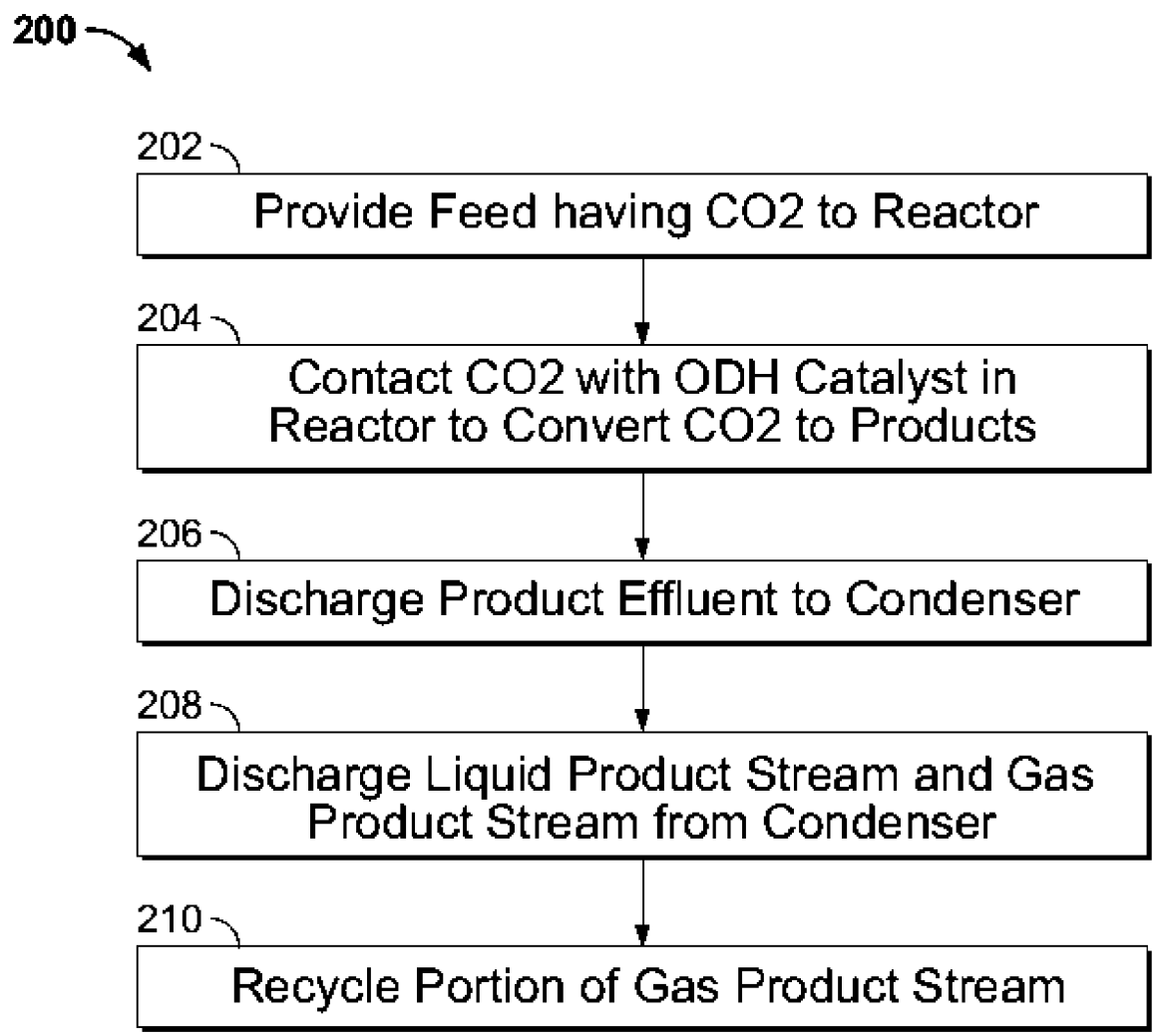
FIG. 2 is a block flow diagram of a method of processing CO2 (e.g., conversion of CO2) with catalyst in a reactor system.

FIG. 2 is a method 200 of processing CO2 (e.g., conversion of CO2) with ODH catalyst, such as in a reactor system having a reactor with ODH catalyst. The reactor system may be characterized as an ODH reactor system because a reactor in the system employs the ODH catalyst and not necessarily that ODH reactions occur or are performed in the reactor or in the CO2 conversion.

At block 202, the method includes providing feed having CO2 to the reactor. The feed includes H2 and optionally water (H2O). If H2O is fed to the reactor, the H2O may be fed as steam (e.g., low pressure steam less than less than or equal to 70 psig) to the reactor in certain embodiments. In implementations, the feed may be heated (preheated) in a heat exchanger (e.g., a shell-and-tube heat exchanger) prior to introduction of the feed to the reactor. Alternatively, the preheating of the feed may be performed via an inert bed before the catalyst bed. Other preheating techniques are applicable. In some implementations, the preheating of the feed may facilitate temperature control in the reactor.

At block 204, the method includes contacting the CO2 with the ODH catalyst in the reactor in the presence of the H2 to convert the CO2 into products, such as acetic acid or CO. Secondary products as byproducts may include, for example, ethane and ethylene. Acetic acid may be produced by hydrogenation of CO2 reaction as given in reaction 1 above. CO may be produced by water gas shift reaction as given in reaction 2 above. As discussed, the presence of H2O in the feed provided to the reactor 102 may inhibit the CO formation by moving (reversing) the water gas shift reaction (reaction 2) to CO2 formation. Thus, the addition of H2O into the feed may promote the production of acetic acid in reaction 1. The absence of H2O in the feed may promote the production of CO.

The method may include maintaining an operating temperature of the reactor at less than 425° C. or less than 400° C. In some implementations, less than 400° C. is implemented to avoid the auto-ignition temperature of acetic acid or to avoid moving equilibrium of the gas shift reaction back to CO2 instead of CO, and the like.

In implementations, the reactor operating pressure may be less than 80 pound per square inch gauge (psig), less than 70 psig, or less than 60 psig. The operating pressure may be in a range of 5 psig to 80 psig. Operating pressures outside of this range are applicable.

Other operating conditions of the reactor in embodiments of the reactor as a tubular fixed-bed reactor may be gas hourly space velocity (GHSV), for example, in the range of 100 hour$^{-1}$ to 5,000 hour$^{-1}$, or 100 hour$^{-1}$ to 10,000 hour$^{-1}$. Linear velocity range of the feed through the reactor may be at least 5 centimeters per second (cm/sec). The linear velocity may be $Q/A*\varepsilon$, where Q is the volumetric flow rate of the feed, A is the cross-sectional flow area (based on inner diameter) of the reactor tube, and $\varepsilon$ is the void space ratio (dimensionless) of the catalyst bed. The void space ratio is the volume of the void space in the catalyst bed divided by the total volume of the catalyst bed. The volumetric flow rate of the feed is the volume of the feed passing through the catalyst bed in units of volume per time.

The reactor operating temperature may be the temperature at which the catalyst (e.g., ODH catalyst) drives CO2 conversion reactions (e.g., CO2 hydrogenation, water gas shift, etc.) in the reactor and which may be maintained by reactor temperature control. The temperature referenced may be the weighted average temperature of the reactor or reactor catalyst bed, e.g., over the temperature profile from reactor inlet to reactor outlet. The reactor operating temperature as referenced may incorporate reactor peak temperatures, and so forth.

At block 206, the method includes discharging a product effluent from the reactor to a condenser. The product effluent may include acetic acid and CO. With presence of H2O in the feed to the reactor, the acetic acid may be the foremost or majority product in the effluent. Additional products may include CO, ethane, and ethylene but at less amounts than acetic acid. With absence of H2O in the feed to the CO2 conversion reactor, the CO may be the foremost or majority product in the effluent. Additional products may include acetic, ethane, ethylene, and methane but at less amounts than CO. In either case (with or without H2O in the feed), the effluent may also include unreacted CO2, unreacted H2, and H2O.

The method may include condensing effluent components, such as acetic acid and water, in the condenser. The condenser may be a heat exchanger, such as a shell-and-tube heat exchanger, plate heat exchanger, plate-and-frame heat exchanger, air-cooled heat exchanger (e.g., finned tube), or other type of heat exchanger. The cooling medium may be, for example, water, air, molten salt, glycol, oil, and so forth.

At block 208, the method include discharging a liquid product stream from the condenser and also discharging a gas product stream from the condenser. Alternatively, a single product stream may be discharged from the condenser and the single product stream separated downstream of the condenser into a liquid product stream and a gas product stream.

The liquid product stream can include acetic acid and H2O. In implementations, the acetic acid can be separated from the H2O and sold. The liquid product stream can also be sent to an ODH reactor system for the conversion of acetic acid to ethylene.

The gas product stream discharging from the condenser can include CO (primary product in absence of H2O feed to the reactor), C2H6, C2H4, unreacted CO2, and unreacted H2. In embodiments, the gas product stream may be sent, for instance, to an ODH system that converts ethane to ethylene. For example, the gas product stream may be introduced into the ODH system (that converts ethane to ethylene) downstream of an acetic acid scrubber in the ODH system. In other embodiments, the gas product stream may be sent to a steam cracker system that converts ethane to ethylene. For example, the gas product stream may be introduced into the steam cracker system downstream of a quench tower in the steam cracker system. In yet other embodiments, the components in the gas product stream may be separated and sent to other systems or sold.

At block 210, the method optionally includes recycling a portion of the gas product stream to the reactor. The recycling of a portion (or all) of the gas product stream may reduce CO2 (including unreacted CO2) discharged from the reactor system. Moreover, the recycle 120 of the gas components may increase conversion of CO2 by the reactor system 100. Optionally, all of the gas product stream may be recycled, such as in the case with little or no interest to recover CO, ethane, and ethylene from the gas product stream. Such implementations may have a focus or interest in production of acetic acid. Yet, if CO production has value, other implementations may recycle some of the gas product stream and send the remaining portion of the gas product stream for recovery of CO, H2, CO2, etc. In those implementations, the recovered CO2 and H2 may be utilized in the feed to the reactor in certain instances. Lastly, in certain embodiments where CO, ethane and ethylene content in the reactor effluent are low such that the CO, ethane and ethylene cannot be readily economically recovered, then the entire gas product stream may be recycled to the reactor, and free CO2 and H2 added for the feed composition to the CO2 conversion reactor.

Applications of the embodiments of the present reactor system that converts CO2 into acetic acid or CO may advance greener ethane-to-ethylene processes by consuming CO2 emissions from those processes. Furthermore, implementations may increase flexibility of steam cracking systems or conventional ODH systems that convert ethane to ethylene to adjust ethylene production versus acetic acid production or CO production. Acetic acid can optionally be converted to other value products, such as ethanol or ethylene, based on market need. CO can optionally be used for syngas generation or utility generation (for example, steam generation). Syngas can then be converted to hydrocarbon-based fuels or methanol.

An embodiment is a method of processing carbon dioxide with catalyst, including contacting carbon dioxide with the catalyst in the presence of hydrogen in a reactor to convert carbon dioxide to acetic acid and carbon monoxide. The method includes discharging a product effluent from the reactor to a condenser heat exchanger. The product effluent includes acetic acid, carbon monoxide, and water. The product effluent may further include ethane, ethylene, unreacted carbon dioxide, or unreacted hydrogen, or any combinations thereof. The method includes condensing the acetic acid and the water in the condenser heat exchanger. The method may include providing a feed having carbon dioxide and hydrogen to the reactor. The method may include heating the feed (e.g., in a heat exchanger) upstream of the reactor. In implementations, the feed includes water, and the selectivity of conversion of carbon dioxide in the reactor favors acetic acid over carbon monoxide, ethane, and ethylene. In other implementation, the feed does not include water, and the selectivity of conversion of carbon dioxide in the reactor favors carbon monoxide over acetic acid, ethane, and ethylene.

EXAMPLES

This Examples are given only as an examples and not meant to limit the present techniques. The Examples were performed with the reactor system 300 depicted in FIG. 3. The reactor 302 in the reactor system 300 is a large-scale laboratory reactor that is a continuous tubular fixed-bed reactor having ODH catalyst. The reactor 302 performed as a CO2 conversion reactor in the Examples.

Figure 3:
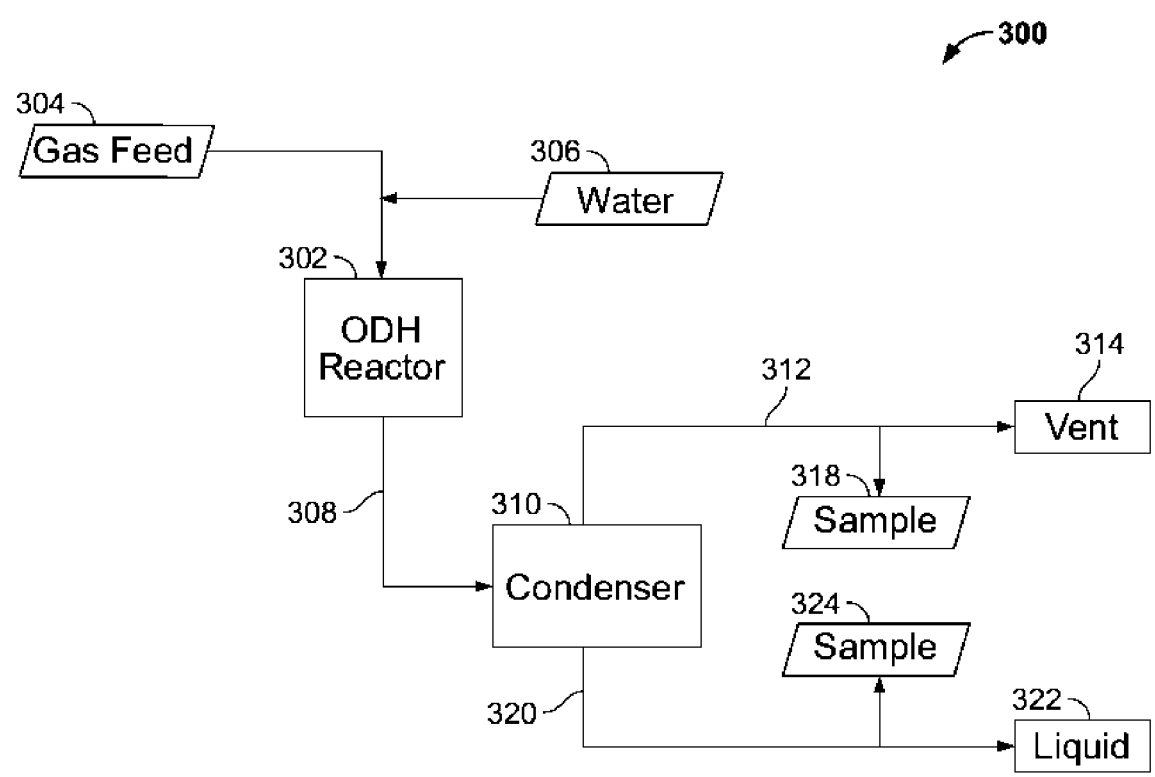
FIG. 3 is a block diagram of a reactor system utilized to perform Examples.

FIG. 3 is the reactor system 300 having the reactor 302 utilized to perform the syntheses over ODH catalyst in the Examples (Examples 1, 2, 3, and 4) that converted CO2 to acetic acid and CO. The reactor 302 is a tubular fixed-bed reactor having two tubes disposed in series and with each tube having a fixed bed of catalyst. The two tubes are constructed of Type 316L stainless steel. The two tubes can each be characterized as two respective tubular fixed-bed reactors but the two tubes were operated collectively in the Examples as a single tubular fixed-bed reactor.

The two tubes each have a heat transfer jacket that receives circulating oil from a closed-loop oil bath for heating or cooling of the two tubes to maintain a desired temperature in the reactor. In the Examples, the reactor temperature was maintained at the temperatures noted in Table 1 and Table 2 below. The temperature of the two tubes was monitored with thermocouples as temperature sensors.

The ODH catalyst in the two fixed beds is $Mo_{1.0}V_{0.37}Te_{0.23}Nb_{0.14}O_{d=4.97}$ with the numerical subscripts indicating molar ratios of the molybdenum, vanadium, tellurium, niobium, and oxygen, as determined by inductively coupled plasma mass spectrometry (ICP-MS). While ICP-MS may not measure oxygen, the oxygen may be determined by the calculation of one hundred percent minus the percentages of Mo, Ve, Te, and Nb. This ODH catalyst is the first low-temperature catalyst described above.

The inside diameter of each tube is 2.1 centimeters (cm) giving a catalyst-bed diameter of 2.1 cm. The catalyst-bed height in the first tube is 128.5 cm. The catalyst bed height in the second tube is 135 cm. The two catalyst beds are "diluted" with a diluent powder. In other words, the catalyst is diluted with diluent powder during the catalyst shaping (e.g., extrusion, pelletizing, spheretizing, etc.) to give the diluted catalyst bed. The mass ratio of diluent powder to catalyst is 1.22. The diluent powder is Versal™ Alumina V-250 manufactured by Honeywell UOP having headquarters in Des Plaines, Illinois, United States of America. The mass of catalyst in the two beds combined is 171 grams. The mass of the diluent in the two beds combined is 209 grams. In preparation for addition to the reactor beds, the catalyst and diluent powder (alumina) are mixed together as powders and then extruded together into a cylindrical shape. The cylindrical extrudate shape has a diameter of about 1.7 millimeter (mm) and a length in the range of 2 mm to 10 mm.

A combined gas feed 304 of CO2 and H2 was fed to the inlet of the reactor 302 from respective gas cylinders of CO2 and H2. The gas cylinders of CO2 and H2 were obtained from Praxair, Inc. (headquarters in Danbury, Conn., USA.) The CO2 content (purity) was greater than 99.9 volume percent. The H2 content (purity) was greater than 99.999 volume percent. The available pressure of the gas cylinders provided motive force for flow of the combined gas feed 304 into the reactor 302. A respective flow valve associated with each gas cylinder gave the desired flow rate of each gas component. Water 306 as feed was introduced into the gas feed 304 flowing to the reactor 302 in Examples 2, 3, and 4, as noted in Table 2 below. The water 306 was fed as liquid water that evaporated into steam at an inlet portion of the reactor 302 having an inert bed and upon initial contact with the catalyst bed. Motive force for conveying the water 306 into the gas feed 304 and to the reactor 302 was by a pump. Table 1 below gives the feed composition in volume percent (vol %) to the reactor 302.

The inlet pressure (psig) at the reactor 302 inlet is given below in Table 1 and Table 2. This reactor 302 inlet pressure is due to the hydraulic backpressure generated by flow of the feed gas through the reactor 302 beds, downstream condenser 310, and associated piping. The gas hourly space velocity (GHSV) and the weight hourly space velocity (WHSV) are given in hour$^{-1}$(h$^{-1}$) in Table 1. The GHSV is the ratio of the volumetric flow rate of the gas feed 304 plus vapor feed generated from evaporation of liquid feed 306 at the inlet of reactor at standard conditions for temperature (25° C.) and pressure (100 kilopascals) to the combined volume of the two fixed-beds of catalyst. The WHSV is the ratio of the weight (mass) flow rate of the total feed (gas feed 304 plus water 306) to the combined weight (mass) of the two fixed-beds of catalyst. The diluent powder is not counted (included) in the basis for the volume or weight of the catalyst bed. The weight and volume of the ODH active phase catalyst (mixed metal oxide) is the basis in the GHSV and WHSV calculations.

The equation for GHSV in the Examples to give the GHSV values presented in Table 1 below is GHSV=Q/V. Q is the volumetric flow rate (also known as volume flow rate, rate of fluid flow, or volume velocity) of the substance or fluid that passes through the catalyst bed in units of volume per time, i.e., is the volume of the substance or fluid that passes through the catalyst bed per unit time. V is the volume of the catalyst bed given in the same units as the volume unit in the volumetric flow rate. In the Examples for the GHSV calculation for determining the GHSV values in Table 1, V is equal to the volume of the active phase of the catalyst bed. In alternate implementations (not given in Table 1), the GHSV can be calculated and expressed with V equal to the volume of the catalyst active phase plus the volume of the catalyst diluent in the catalyst bed.

The equation for WHSV in the Examples to give the WHSV values presented in Table 1 below is WHSV=μ/m, where p is the mass flow rate of the substance or fluid that passes through the catalyst bed and is in units of mass per time, i.e., is the mass of substance or fluid that passes through the catalyst bed per unit time. The variable m is the mass of the catalyst bed given in the same units as the mass unit in the mass flow rate. In the Examples for the WHSV calculation for determining the WHSV values in Table 1, m is equal to the mass of the active phase of the catalyst bed. In alternate implementations (not given in Table 1), the WHSV can be calculated and expressed with m equal to the mass of the catalyst active phase plus the mass of the catalyst diluent in the catalyst bed.

The product effluent 308 discharged from the reactor 302 to a condenser 310, which condensed acetic acid and water in effluent 308. The cooling medium in the condenser 310 was distilled water. The condenser 310 is a shell-and-tube heat exchanger with product gas on the tube side and the distilled water on the shell side. A product gas stream 312 discharged from the condenser 310 to a vent system 314. A sample syringe was utilized to collect a gas sample 318 of the product gas stream at a sample point downstream of the condenser 310. A liquid product stream 320 discharged from the condenser 310 to a liquid collection system 322. A liquid sample 324 of the liquid product stream 320 was obtained.

The CO2 conversion in carbon atom percent (C-atom %) and the selectivity (C-atom %) as normalized given in Table 2 are based on analysis of the gas sample 318 and the liquid sample 322. Acetic acid was the dominant product when H2O-CO2-H2 feed mixture was utilized. CO was a dominant product when CO2-H2 feed mixture was utilized. When the H2O-CO2-H2 feed mixture was utilized (in all operating conditions), the CO, C2H6, and C2H4 were ranked as the 2nd, 3rd, and 4th dominant products, respectively. Additionally, when the H20-CO2-H2 feed mixture was utilized, an increase in reactor temperature or reactor inlet pressure gave an increase in acetic-acid selectivity and yield. In those cases, the yield is the CO2 conversion multiplied by the acetic-acid selectivity.

TABLE 1

Reactor Operating Conditions and Feed Composition

| Example | GHSV (h$^{-1}$) | WHSV (h$^{-1}$) | Reaction T (° C.) | Reactor Inlet P (psig) | Feed (vol %) | | |
|---|---|---|---|---|---|---|---|
| | | | | | H2O | H2 | CO2 |
| 1 | 459 | 0.58 | 325 | 17 | 0 | 50 | 50 |
| 2 | 459 | 0.53 | 325 | 15 | 40 | 30 | 30 |
| 3 | 459 | 0.53 | 320 | 15 | 40 | 30 | 30 |
| 4 | 459 | 0.53 | 320 | 51 | 40 | 30 | 30 |

TABLE 2

Catalyst Activity and Product Distribution

| Example | Reaction T (° C.) | Reactor Inlet P (psig) | CO2 Conversion (C-atom %) | Selectivity (C-atom %) - normalized | | | |
|---|---|---|---|---|---|---|---|
| | | | | C2H6 | C2H4 | CO | CH4 | Acetic Acid |
| 1 | 325 | 17 | 11.6 | 2 | 1 | 95 | 1 | 1 |
| 2 | 325 | 15 | 1.3 | 8 | 3 | 14 | 0 | 74 |
| 3 | 320 | 15 | 0.8 | 10 | 0 | 29 | 0 | 61 |
| 4 | 320 | 51 | 0.7 | 12 | 1 | 11 | 0 | 76 |

Lastly, Aspen Plus® software (version 8.6) was utilized to calculate the heat of reaction of Example 2. In the simulation, an Aspen Plus® RYield reactor block was utilized to simulate the net heat of reaction as 161 kilojoules (KJ) per mole of CO2 converted. This implies that the reaction in Example 2 is endothermic. Therefore, a practice may be to provide a preheated feed to this reactor or heat the reactor body to accommodate the net reaction. Aspen Plus® software is available from Aspen Technology, Inc. headquartered in Bedford, Massachusetts, USA. It should be noted that variations of the balance of reactions in the reactor, including on scale-up to industrial scale, may provide for the net of the reactions in the reactor to be exothermic. Therefore, a practice in some instances may be to cool the reactor, such as by flowing a cooling medium through a heat-transfer jacket of the reactor. Lastly, the reactor in particular implementations might switch between endothermic operation and exothermic operation, depending on the feed composition and operating conditions of the reactor.

FIG. 4 is integrated systems 400 including the reactor system 100 (FIG. 1) that converts CO2 to acetic acid or CO. The integrated systems 402 also includes a system 402 that converts ethane to ethylene. The system 402 may be, for example, a conventional ODH reactor system or a steam cracker furnace system. The system 402 includes a component 404 that performs the conversion of ethane to ethylene. The component 402 may be an ODH reactor that receives ethane and contacts the ethane on ODH catalyst in the presence of oxygen to convert the ethane to ethylene (e.g., via an ODH reaction). Such an ODH reactor may generate byproducts such as acetic acid, CO, and CO2 but ethylene is the primary product. The component 402 may be a steam cracking furnace that receives ethane as feed and converts the ethane to ethylene via steam and high temperature.

The system 400 generates CO2 emissions 406 in the conversion of ethane to ethylene. The CO2 emissions 406 may be collected as waste or sent to the environment. In the illustrated embodiment, the system 400 diverts some of the CO2 emissions 406 as feed 106 to the CO2 conversion reactor system 100. Therefore, the system 400 reduces CO2 emissions 406 by diverting a portion of the CO2 emissions to the CO2 conversion reactor system 100. The source of the CO2 may be, for example, from flue gas of a steam cracker furnace, or from an amine tower in the steam cracker furnace system or in the conventional ODH system.

As discussed, the CO2 conversion reactor system 100 may add H2 and optionally H2O to the feed 106, as discussed above. The reactor system 100 may convert the CO2 to acetic acid or CO and other secondary products. In the conversion of the CO2, the reactor system 100 may provide liquid components 116 that include water and acetic acid. Acetic acid can be a primary product if H2O is added to the feed 106. The reactor system 100 may give gas components 118 that can include CO (product), C2H6 (secondary product), C2H4 (secondary product), CO2 (unreacted feed 106), and H2 (unreacted H2 added to feed 106). The CO can be a primary product if H2O is not added to the feed 106.

An embodiment is a method of processing carbon dioxide in a reactor system, including contacting carbon dioxide with catalyst in presence of hydrogen in a reactor to convert carbon dioxide to acetic acid, carbon monoxide, ethane, and ethylene. In certain implementations, the reactor is a fixed-bed reactor having the catalyst (e.g., ODH catalyst) in a fixed bed. The method may include maintaining an operating temperature of the reactor at less than 425° C. or less than 400° C. The method includes discharging an effluent from the reactor to a condenser (a heat exchanger). The effluent includes acetic acid, carbon monoxide, ethane, ethylene, water, carbon dioxide, and hydrogen. The method includes condensing the acetic acid and the water in the condenser (e.g., a heat exchanger, quench tower, etc.). The method may include feeding water to the reactor, wherein selectivity of conversion of carbon dioxide in the reactor favors acetic acid over carbon monoxide, ethane, and ethylene. On the other hand, the method may include not feeding water to the reactor, wherein selectivity of conversion of carbon dioxide in the reactor favors carbon monoxide over acetic acid, ethane, and ethylene.

Another embodiment is a system to convert carbon dioxide into products. The system includes a reactor having an ODH catalyst to convert carbon dioxide in the presence of hydrogen into at least acetic acid and carbon monoxide, and discharge a product effluent including at least acetic acid, carbon monoxide, water, and unreacted carbon dioxide. The system includes a condenser (e.g., shell-and-tube heat exchanger) to receive the product effluent and condense acetic acid and water, and discharge a liquid product stream including at least acetic acid and water and a gas product stream including at least carbon monoxide and unreacted carbon dioxide. The system may include a recycle conduit to convey at least a portion of the gas product stream to the reactor. The system may include a preheater (e.g., shell-and-tube heat exchanger) to heat feed to the reactor, wherein the feed includes at least carbon dioxide and hydrogen.

A number of implementations have been described. Nevertheless, it will be understood that various modifications may be made without departing from the spirit and scope of the disclosure.

INDUSTRIAL APPLICABILITY

Catalytic conversion of carbon dioxide into acetic acid or carbon monoxide.

The invention claimed is:

1. A method of processing carbon dioxide, comprising:
    contacting carbon dioxide with catalyst in presence of hydrogen in a reactor to convert carbon dioxide to acetic acid, carbon monoxide, ethane, and ethylene;
    discharging a product effluent from the reactor to a condenser heat exchanger, the product effluent comprising acetic acid, carbon monoxide, ethane, ethylene, and water, wherein the condenser comprises a condenser heat exchanger or a quench tower; and
    condensing the acetic acid and the water in the condenser,
    wherein the catalyst comprises oxidative dehydrogenation (ODH) catalyst.

2. The method of claim 1, comprising providing a feed to the reactor, the feed comprising the carbon dioxide and the hydrogen.

3. The method of claim 2, comprising heating the feed upstream of the reactor.

4. The method of claim 3, wherein heating the feed comprises heating the feed in a heat exchanger upstream of the reactor.

5. The method of claim 2, wherein the feed comprises water, and wherein selectivity of conversion of carbon dioxide in the reactor favors acetic acid over carbon monoxide.

6. The method of claim 1, comprising feeding water to the reactor, wherein selectivity of conversion of carbon dioxide in the reactor favors acetic acid over carbon monoxide, ethane, and ethylene.

7. The method of claim 1, wherein selectivity of conversion of carbon dioxide in the reactor favors carbon monoxide over acetic acid, ethane, and ethylene in absence of feeding water to the reactor.

8. A method of processing carbon dioxide in reactor system, comprising:
contacting carbon dioxide with catalyst in presence of hydrogen in a reactor to convert carbon dioxide to acetic acid, carbon monoxide, ethane, and ethylene;
discharging an effluent from the reactor to a condenser, the effluent comprising acetic acid, carbon monoxide, ethane, ethylene, water, carbon dioxide, and hydrogen; and
condensing the acetic acid and the water in the condenser, wherein the condenser comprises a heat exchanger.

9. The method of claim 8, comprising feeding water as steam to the reactor, wherein selectivity of conversion of carbon dioxide in the reactor favors acetic acid over carbon monoxide, ethane, and ethylene.

10. The method of claim 8, comprising not feeding water to the reactor, wherein selectivity of conversion of carbon dioxide in the reactor favors carbon monoxide over acetic acid, ethane, and ethylene.

11. The method of claim 8, comprising maintaining an operating temperature of the reactor at less than 400° C., wherein the catalyst comprises oxidative dehydrogenation (ODH) catalyst.

12. The method of claim 8, wherein the reactor comprises a fixed-bed reactor having the catalyst in a fixed bed.

13. The method of claim 8, wherein the catalyst comprises a mixed metal oxide having formula $Mo_aV_bTe_cNb_dPd_eO_f$, where a, b, c, d, e, and f subscripts are relative atomic amounts of elements Mo, V, Te, Nb, Pd, O, respectively, and when a=1, b=0.01 to 1.0, c=0.01 to 1.0, d=0.01 to 1.0, 0.00≤e≤0.10, and f is a number to satisfy at least the valence state of corresponding elements in the catalyst.

* * * * *